: US010538731B2

(12) United States Patent
Casset et al.

(10) Patent No.: US 10,538,731 B2
(45) Date of Patent: Jan. 21, 2020

(54) DEVICE FOR MANIPULATING BIOLOGICAL CELLS USING A VIBRATING SUPPORT

(71) Applicant: Commissariat a L'Energie Atomique et aux Energies Alternatives, Paris (FR)

(72) Inventors: Fabrice Casset, Tencin (FR); Arnaud Millet, Saint Egreve (FR)

(73) Assignee: Commissariat a L'Energie Atomique et aux Energies Alternatives, Paris (FR)

( * ) Notice: Subject to any disclaimer, the term of this patent is extended or adjusted under 35 U.S.C. 154(b) by 94 days.

(21) Appl. No.: 15/046,803

(22) Filed: Feb. 18, 2016

(65) Prior Publication Data
US 2016/0244715 A1 Aug. 25, 2016

(30) Foreign Application Priority Data

Feb. 19, 2015 (FR) ..................................... 15 51409

(51) Int. Cl.
| | |
|---|---|
| C12M 1/00 | (2006.01) |
| C12M 3/00 | (2006.01) |
| B01L 3/00 | (2006.01) |
| C12M 3/06 | (2006.01) |
| C12M 1/26 | (2006.01) |
| C12M 1/12 | (2006.01) |

(52) U.S. Cl.
CPC ............ *C12M 47/04* (2013.01); *C12M 23/16* (2013.01); *C12M 23/20* (2013.01); *C12M 25/02* (2013.01); *C12M 33/08* (2013.01)

(58) Field of Classification Search
CPC .............................. C12M 35/04; C12M 35/00
See application file for complete search history.

(56) References Cited

U.S. PATENT DOCUMENTS

| 6,759,245 B1 * | 7/2004 | Toner .................. A61M 1/3472 |
| | | 435/284.1 |
| 2005/0153437 A1 * | 7/2005 | Kishida .................. C12M 35/04 |
| | | 435/289.1 |
| 2006/0062698 A1 | 3/2006 | Foster et al. |

(Continued)

FOREIGN PATENT DOCUMENTS

| EP | 2 747 452 A1 | 6/2014 | |
| JP | WO-2014017481 A1 * | 1/2014 | ............... C12N 5/00 |

(Continued)

OTHER PUBLICATIONS

Additional Preliminary Search Report dated Apr. 21, 2016 in French Patent Application No. FR 1551409 (with English translation of categories of cited documents).

(Continued)

Primary Examiner — Nathan A Bowers
(74) Attorney, Agent, or Firm — Oblon, McClelland, Maier & Neustadt, L.L.P.

(57) ABSTRACT

Device for sorting living cells, comprising at least one support including a surface having adherence properties with respect to said type of living cells, actuators capable of making said surface vibrate at at least one given frequency and a controller for controlling the actuators such that the surface vibrates at a frequency causing the detachment of at least one type of living cells.

18 Claims, 8 Drawing Sheets

(56) References Cited

U.S. PATENT DOCUMENTS

| | | | |
|---|---|---|---|
| 2008/0245745 A1 | 10/2008 | Ward et al. | |
| 2009/0298153 A1* | 12/2009 | Martin | C12M 23/34 435/173.9 |
| 2011/0024335 A1 | 2/2011 | Ward et al. | |
| 2012/0003709 A1* | 1/2012 | Fukui | C12M 23/04 435/173.9 |
| 2012/0273357 A1 | 11/2012 | Katsumoto et al. | |
| 2012/0276622 A1 | 11/2012 | Wu et al. | |
| 2013/0213488 A1 | 8/2013 | Weitz et al. | |
| 2014/0030805 A1* | 1/2014 | Kasuto | C12N 5/0075 435/366 |
| 2014/0357506 A1* | 12/2014 | Singh | C12N 5/0696 506/9 |
| 2016/0030950 A1 | 2/2016 | Katsumoto et al. | |

FOREIGN PATENT DOCUMENTS

| | | | | |
|---|---|---|---|---|
| WO | WO 2007/053281 A2 | 5/2007 | | |
| WO | WO 2009/018847 A1 | 2/2009 | | |
| WO | WO 2012/027366 A2 | 3/2012 | | |
| WO | WO 2012/140519 A2 | 10/2012 | | |
| WO | WO 2014/037862 A1 | 3/2014 | | |
| WO | WO-2015071830 A1 * | 5/2015 | | B01D 33/0353 |

OTHER PUBLICATIONS

European Search Report dated Jun. 22, 2016 in Patent Application No. 16156161.8 (with English translation of categories of cited documents).

Zhonglan Tang, et al., "Shear stress-dependent cell detachment from temperature-responsive cell culture surfaces in a microfluidic device" Biomaterials, vol. 33, No. 30, XP055263558, Jul. 20, 2012, pp. 7405-7411.

French Preliminary Search Report dated Dec. 10, 2015 in French Application 15 51409, filed Feb. 19, 2015 (with English Translation of Categories of Cited Documents).

Dorothee Debavelaere-Callens et al. "On the Use of Ultrasounds to Quantify the Longitudinal Threshold Force to Detach Osteoblastic Cells from a Conditioned Glass Substrate", Biomolecular Engineering, vol. 24, 2007, 5 pages.

Wesley C. Chang et al. "Biomimetic Technique for Adhesion-Based Collection and Separation of Cells in a Microfluidic Channel", Lab Chip, vol. 5, 2005, 10 pages.

Keon Woo Kwon et al. "Label-Free, Microfluidic Separation and Enrichment of Human Breast Cancer Cells by Adhesion Difference", Lab Chip, vol. 7, 2007, 8 pages.

Evgenia Mandrusov et al. "Membrane-Based Cell Affinity Chromatography to Retrieve Viable Cells", Biotechnol. Prog. vol. 11, 1995, 6 pages.

Aaron Sin et al. "Enrichment Using Antibody-Coated Microfluidic Chambers in Shear Flow: Model Mixtures of Human Lymphocytes", Biotechnology and Bioengineering, vol. 91, No. 7, 2005, 11 pages.

F. Casset et al. "Piezoelectric Membrane Actuator Design", 2011 12$^{th}$ Intl. Conf. on Thermal, Mechanical & Multi-Physics Simulation and Experiments in Microelectronics and Microsystems, 2011, 3 pages.

European Office Action dated Mar. 6, 2019 in European Application No. 16 156 161.8, 4 pages.

* cited by examiner

| Mode | 1 | 9 | 17 | 25 | 51 | 74 |
|---|---|---|---|---|---|---|
| (kHz) | 5,3 | 7,98 | 11,28 | 15,23 | 25,27 | 38,65 |

FIG.4

| i | j | $\lambda_{ij}$ | Deformed | i | j | $\lambda_{ij}$ | Deformed |
|---|---|---|---|---|---|---|---|
| 0 | 0 | 10.22 | | 3 | 1 | 111 | |
| 1 | 0 | 21.26 | | 1 | 2 | 120.1 | |
| 2 | 0 | 34.88 | | 2 | 2 | 153.8 | |
| 0 | 1 | 39.77 | | 0 | 3 | 158.2 | |
| 3 | 0 | 51.04 | | 3 | 2 | 190.3 | |
| 1 | 1 | 60.82 | | 1 | 3 | 199.1 | |
| 4 | 1 | 69.67 | | 2 | 3 | 242.7 | |
| 2 | 1 | 84.58 | | 3 | 3 | 289.2 | |
| 0 | 2 | 89.10 | | | | | |

FIG.8

DEVICE FOR MANIPULATING BIOLOGICAL CELLS USING A VIBRATING SUPPORT

TECHNICAL FIELD AND PRIOR ART

The present invention relates to a device for manipulating biological cells using a vibrating support and to a device for sorting biological cells. The possibility of sorting biological cells from a heterogeneous mixture is a major issue in biomedicine.

There exist two techniques that are mainly used:
sorting by flow cytometry (Fluorescence Activated Cell Sorting or FACS), this technique is based on the fluorescent marking of cells using specific colorants or fluorescent antibodies directed against surface antigens. The light scattering and fluorescence properties make it possible to select the population(s) of interest. This technique offers the possibility of selection with high purity but at the price of costly equipment.
isolation using magnetic beads (Magnetic Activated Cell Sorting or MACS), this technique is based on the use of antibodies directed against surface antigens coupled to magnetic beads enabling a cell rate which can exceed flow cytometry at the price of lower purity.

These two techniques are widely used but necessitate the use of cells in suspension, requiring fine tuning concerning the concentration of the antibody, the density of cells, the size of the magnetic beads and require the existence of specific markers expressed at the surface of the cell enabling sorting. Yet these markers may turn out to be inexistent for certain types of cells, for example for cancerous cells which do not always have identified specific surface antigens.

Consequently, these sorting or isolation techniques are not applicable to all cells.

Other techniques exist enabling sorting without prior marking, for example techniques using size and density (CCE or Counterflow Centrifugal Elutriation) and those using dielectrophoretic fractionation. On the other hand, they do not enable sufficient resolution to be reached. Moreover, in the particular case of dielectrophoresis, the survival of cells may not be assured.

Another physical parameter is used to sort cells, namely cell adherence with respect to a surface, which depends on the studied cell type, the adherence surface and the biochemical environment of the cell. This physical parameter can prove to be very discriminating for cell sorting without requiring prior marking.

This physical parameter is used in cell affinity chromatography devices comprising a microfluidic chamber, in which a surface is functionalised. A fluid transporting cells flows on a functionalised surface. The cells adhere to the surface according to their affinity with the surface.

The functionalisation of the surface may take place chemically by formation of a functionalisation layer or by nanostructuring. The document Chang et al *Biomimetic technique for adherence-based collection and separation of cells in a microfluidic channel. Lab Chip* 2005, 5, 64-73 describes such a device. The document Mandrusov et al. *Membrane-based cell affinity chromatography to retrieve viable cells. Biotechnol. Prog.* 1995, 11, 208-213 also describes a cell separation method using affinity with a surface.

The document Sin et al. *Enrichment using antibody-coated microfluidic chambers in shear flow: model mixtures of human lymphocytes. Biotechnology & Bioengineering,* VOL. 91, NO. 7, Sep. 30, 2005 pages 816-826 describes the use of micro-fluidic circuits with surfaces functionalised by antibodies. The document Kwon et al. *"Label-free, microfluidic separation and enrichment of human breast cancer cells by adherence difference" Lab Chip* 2007, 7, 1461-1468 describes the use of micro-fluidic circuits with surfaces functionalised by structured surfaces.

These devices make it possible to collect cells having an affinity with the functionalised surface, but the recovery of said cells may pose a problem. The recovery may be obtained by applying a shear stress using a liquid so as to take off the cells. Said devices do not enable the application of a uniform shear force, notably on the edges of the microfluidic chambers, thereby preventing efficient sorting.

DESCRIPTION OF THE INVENTION

It is consequently an aim of the present invention to offer a device offering facilitated manipulation of biological cells and which can be discriminating.

It is an additional aim of the present invention to offer a cell sorting device offering improved efficiency, notably in the sorting of cancerous cells.

The aforementioned aim is attained by a device implementing a support and means of making the support vibrate according to at least one frequency so as to apply an inertial force to the cells which have adhered to the support which is capable of taking them off. The force of adherence to a given surface makes it possible to characterise one type of cells with respect to another. It is thus possible to modify the adherence of the cells to the support by modifying the vibration frequency and take a desired type of cell off.

In other words, a device is formed having different adherence properties vis-à-vis different cell types, said different cell types are selected by transmitting to them a force which is sufficient to detach a given cell population from the support.

For example, the support is made to vibrate by means of a piezoelectric actuator.

For example, a fluid containing the cells of interest is made to circulate on a support, the cells of interest and others adhere to the support. By applying one or more vibrations of given frequencies, it is then possible either to detach only the cells of interest or only the other cells. By only conserving the cells of interest on the support, it is possible to accumulate the cells of interest on the support.

Advantageously, the support surface(s) may be functionalised to modify the adherence forces of the cells on the surface(s).

The subject matter of the present invention is then a device for manipulating one or more types of biological cell distinguishable from their adherence properties, comprising:
at least one support having a reception surface enabling the adherence of said cells,
at least one actuator capable of making said surface vibrate at at least one given frequency, and
means for controlling said actuator such that the surface vibrates at a frequency causing the detachment of at least one type of biological cells.

The given frequency can be a natural frequency of a suspended membrane which is the support.

In the present application, "type of cells" is taken to mean either a cell species or a particular biological state within a same species.

Thanks to this device, the detachment of at least one type of biological cells notably enables their distinction.

In the case of biological cells of several types, the control means can control the actuator such that it can make said surface vibrate at several given frequencies, each of the frequencies being selected so as to cause the detachment of at least one of the types of biological cells.

Preferably, the frequency or the frequencies is or are selected such that the waves generated correspond to deformations of the surface of the order of the size of the biological cells or smaller than the size of the biological cells.

A device in which the waves generated correspond to deformations of the surface greater than the size of the biological cells does not go beyond the scope of the present invention.

In an example of embodiment, the device is capable of making the surface vibrate at several frequencies, said different frequencies being applied preferably sequentially.

All or part of the surface may be functionalised so as to modify the adherence force of the type(s) of biological cells with respect to the non-functionalised surface.

In an example of embodiment, the support is formed by a suspended membrane. The largest dimension of the membrane may be comprised between several μm and several hundreds of μm, preferably between 5 μm and 20,000 μm.

In another example of embodiment, the support is formed by a plate, for example a glass plate, the sides of which measure for example between several hundreds of μm to several cm.

Advantageously, the control means control the actuator such that the support vibrates in a Lamb mode.

Several actuators may be distributed on or under the surface of the support. The control means can control the actuators such that they make the surface of the support vibrate according to a different mode.

The actuator or the actuators may be selected from piezoelectric, ferroelectric, electrostatic, magnetic or thermal actuators. It is possible to provide to use different types of actuator on the same support.

In an example of embodiment, the actuator is formed on one face of the support opposite to the surface intended to enter into contact with the biological cells.

In a very advantageous manner, the manipulation device is a MEMS and/or NEMS device.

The subject matter of the present invention is also a device for sorting biological cells comprising at least one device for manipulating biological cells according to the invention.

The subject matter of the present invention is also a microfluidic device comprising at least one device for manipulating biological cells according to the invention or a sorting device according to the invention, comprising at least one supply inlet with a solution comprising at least one type of biological cells and at least one evacuation outlet, the support being arranged between the supply inlet and the evacuation outlet.

The microfluidic device may be used to carry out the sorting of cells or for example for the cleaning of the support surface.

The subject matter of the present invention is also a method for sorting different types of biological cells contained in a solution implementing the sorting device according to the invention, comprising the steps:
  bringing the solution containing the different types of biological cells into contact with the surface of the support,
  adherence of the cells of different types on the surface of the support,
  making the surface vibrate at at least one given frequency so as to detach at least one of the types of cells,
  evacuation of the detached cells.

BRIEF DESCRIPTION OF THE DRAWINGS

The present invention will be better understood on the basis of the description that follows and the appended drawings in which:

FIG. 4 is a representation of the support of FIG. 3 in different vibration modes, FIG. 8 represents possible vibration modes of a circular membrane.

DETAILED DESCRIPTION OF PARTICULAR EMBODIMENTS

The description that follows mainly pertains to the application of the invention to the sorting of living cells but the present invention may have other applications that will be described hereafter.

Figure 1:
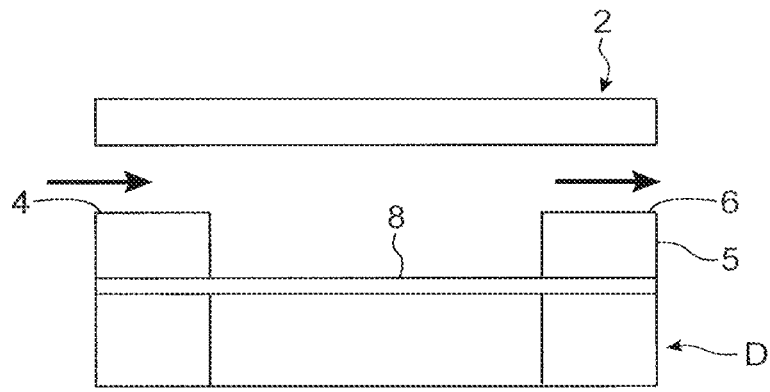
FIG. 1 is a schematic representation of a cell sorting device implementing the invention.

In FIG. 1 may be seen a schematic representation of an example of a cell sorting device implementing the present invention.

In the example represented, the cell sorting device comprises a housing 2 provided with a fluid supply inlet 4 formed in a lateral wall 5 of the housing and a fluid evacuation outlet 6 formed in the lateral wall 5 of the housing and a bottom 8. The supply inlet 4 and the evacuation outlet 6 are arranged with respect to the bottom 8 such that the flux of fluid flows on the bottom of the inlet 4 to the outlet 6.

It is possible to envisage arranging the device in a temperature controlled enclosure.

The bottom 8 is formed by a device D offering variable adherence properties for at least one type of cell.

The device D comprises a support, in the example represented formed by a membrane suspended 12 at the lateral wall of the housing. The device also comprises at least one actuator capable of making the membrane vibrate according to a given frequency. In the example represented, the device comprises two actuators 14, 16 implementing a ferroelectric material, for example PZT, one of the actuators serves for moving the membrane upwards and the other actuator serves for moving the membrane downwards. In the case where a piezoelectric material is implemented, a single actuator is sufficient to assure upwards and downwards movements, since a piezoelectric material expands and contracts according to the sign of the applied voltage.

Figure 2:
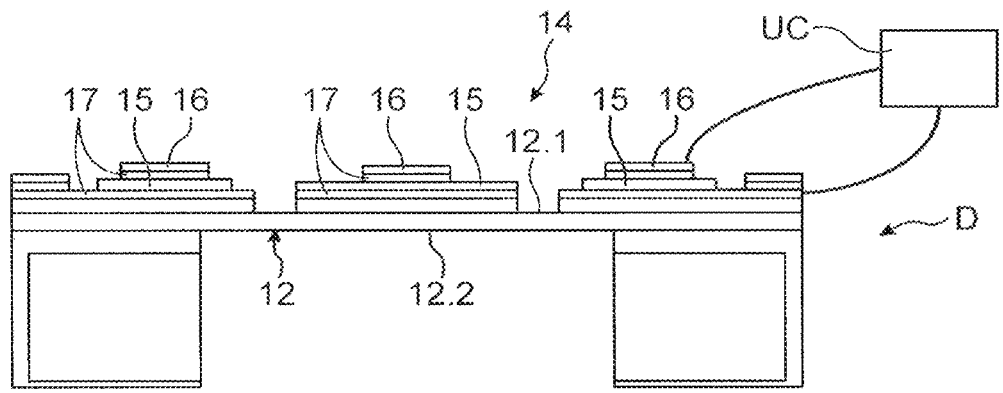
FIG. 2 is a sectional view of an example of support which can be implemented in the device of FIG. 1.

The device D is represented in an isolated manner in FIG. 2, said device being upturned around with respect to the representation of FIG. 1.

The membrane 12 has a circular shape, the actuator 14 is a ferroelectric actuator and is arranged substantially at the centre of the membrane 12 on one face 12.1 opposite to that 12.2 situated in the housing and intended to enter into contact with the fluid. The actuator 16 is also a ferroelectric actuator of annular shape and lining the outer edge of the external surface 12.1 of the membrane 12.

The inner surface 12.2 is such that it has adherence properties with respect to one or more types of cells. The surface 12.2 is for example made of glass, silicon or any semi-conductor material.

In a variant, it could be envisaged that it is the side of the device bearing the actuator(s) which have adherence properties with respect to one or more types of cells; means for electrically isolating the actuators from the fluid containing the cells could then be provided, for example an electrical insulating layer.

The actuators 14, 16 comprise a ferroelectric material 15 and two electrodes 17 on either side of the material 15 making it possible to apply to said material 15 an electric field on command, which causes a deformation in the plane of the material and thus an out-of-plane deformation of the membrane with which it is integral, by bimetal effect. By applying an alternating voltage to the electrodes 17, the membrane vibrates 12 at the resonance frequencies of the different natural modes of the membrane.

The optimisation of such actuators is described in the document F. Cosset et al, "*Piezoelectric membrane actuator design*", 12*th Int. Conf. On Thermal, Mechanical and Multiphysics Simulation and Experiments in Microelectronics and Microsystems* (*IEEE Eurosime*), 18-20 April 2011, pp. 1-5.

In a variant, the membrane could be of square or rectangular shape.

In a variant, a single actuator could be implemented.

Furthermore, the actuator(s) may be electrostatic, magnetic, thermal type actuators, etc.

In a variant, it could be envisaged that it is the side of the device bearing the actuator(s) which have adherence properties with respect to one or more types of cells; means for electrically isolating the actuators from the fluid containing the cells could then be provided, for example an electrical insulation layer.

Each type of biological cells may be characterised by a value of adherence force with respect to a given surface and the culture conditions. The adherence forces of the different cell types are generally comprised between 1 nN and 500 nN.

The temperature, the pH, the $O_2$ pressure and the presence of serum in the culture medium can have an impact on the adherence. For example, a temperature below 37° C. for human cells reduces the adherence forces. The presence of serum in the culture medium favours for its part adherence but the quantitative aspect is highly variable from one cell type to another. The impact on the adherence of the culture conditions depends on the type of surface considered.

Examples of adherence force $F_{adh}$ for different types of cell will now be given:
  for fibroblasts (NIH/3T3) on non-functionalised glass, $F_{adh}$ is of the order of 369 nN;
  for L929 murine fibroblasts on a plastic cell culture, $F_{adh}$ is comprised between 310 nN and 390 nN;
  for human cervical carcinoma cells, which are cancerous cells, on a functionalised surface with fibronectin, $F_{adh}$ is of the order of 204 nN;
  for normal epithelial cells of the cervix, $F_{adh}$ is of the order of 100 nN;
  for other cell types, $F_{adh}$ is weaker, for example for keratinocytes $F_{adh}$ is of the order of 20 nN.

The operation of the sorting device will now be described. A solution containing at least the cells of interest is made to circulate between the inlet 4 and the outlet 6, both the cells of interest and the other cells contained in the solution adhere to the surface 12.2 on account of the selection of the material thereof.

Then, the membrane 12 is made to vibrate at a given frequency which transmits an acceleration to the cells. The type of cells for which said acceleration assures disbonding disbonds and is evacuated by the fluid. It may be decided to detach either the cells of interest and to recover the fluid coming out of the evacuation outlet, or to detach the other cells. In the latter case, by resuming several times the fixation of cells of interest and the detachment of cells not of interest, it is possible to accumulate the cells of interest on the membrane.

The frequency increases with the adherence force. It will be understood that the cells having the lowest adherence force are disbonded firstly with respect to all the types of cells bonded onto the surface and that the cells are disbonded in the order of their increasing adherence force.

In a very advantageous manner, the surface of the support may be functionalised either by forming a functionalisation layer for example by deposition, or by structuring the surface. The functionalisation makes it possible to modify the adherence forces vis-à-vis certain types of cells in a discriminatory manner and thus to optimise the resolution power of the device.

It may be a chemical functionalisation of the surface which may take place for example with molecules of the extracellular matrix such as fibronectin, collagen I, but also cationic compounds such as Poly-L-Lysine or instead with antibodies. It may be a physical functionalisation, in which case the microstructuring of the surface is modified. A physical functionalisation and a chemical functionalisation may be envisaged.

It may be envisaged that the adherence forces between two cell types are inversed by the functionalisation of a surface, compared to the situation without functionalisation.

It will now be explained how the frequency at which a type of cells disbonds from a given surface may be determined.

By estimating the mass for example of a eukaryote cell at around 1 ng, it is possible to evaluate the orders of magnitude of frequencies of vibration of the membrane assuring disbonding of the cells. The biological cell is considered as a passive mechanical system in a first approximation.

The frequency may be written:

$$f \approx \frac{1}{2\pi} \sqrt{\frac{F_{adh}}{m\delta}} \quad (I)$$

With m the mass of a cell of around 1 ng,
  $F_{adh}$ the adherence force of the cell for a given surface,
  δ the amplitude of vibration which can be modulated between 0.1 μm and 10 μm.

The order of magnitude of the frequencies to apply to the membrane is then comprised between around 50 Hz and around 10 kHz.

Furthermore, since the membrane is intended to be used in flow in liquid medium, it applies shear forces to the cells which have adhered to the membrane which could disbond the cells and interfere with the mechanism of sorting by vibration.

The shear forces τ may be written in the following manner:

$$\tau = \eta (\delta v\_II)/\delta z \sim \eta \omega \delta / \delta = \eta \omega$$

With η the viscosity of the medium, this is estimated at around $10^{-3} m^2 s^{-1}$, $v_{//}$ the velocity parallel to the surface which is estimated to be of the same order of magnitude as the velocity of movement of the plate in incompressible regime for a wetting fluid and ω the frequency of vibration of the plate.

The surface of a cell on which the force is going to be applied is close to 10 µm².

The order of magnitude of the shear forces applied by the fluid is then comprised between 10 pN and 1 nN, this is less than the adherence forces of the aforementioned cells and for cancerous cells, such as for example the MCF-7 breast cancer cell line on nanostructured PDMS, the adherence force is close to 7 nN. Thus there is no risk that the cells are taken off by the liquid and not by the vibration of the membrane.

The preceding estimation is based on the hypothesis that the wavelength of the first mode of vibration of a circular membrane is at least of the order of magnitude of the characteristic size of the cell.

But is will be understood that the invention is not limited either to the first mode of vibration, or to the implementation of a circular membrane as will be explained below or waves of which the wavelength is at least of the order of magnitude of the characteristic size of the cell. The invention may advantageously implement one or more modes of which the waves have wavelengths below the size of the cell, for example by working at frequencies of the order of the MHz, the wavelength is of the order of µm. Thus, these short wavelengths are going to correspond to deformations of the membrane over planar dimensions comparable to the dimensions of a cell, or even less. Such modes make it possible very advantageously to take the cell focal adherence points off. The taking off of the focal adherence points has the advantage of considerably increasing the chances of cell survival during taking off. In fact, vibration modes entailing an inertial force on the totality of the cell body can lead to membrane damage for high amplitudes and/or frequencies.

In the case of a device comprising a circular membrane with piezoelectric actuation, the resonance frequency for out-of-plane vibration modes may be determined by analytical calculation, such as for example the use of the following equation $$f_r = \frac{\lambda_n^2 t}{2\pi r^2} \sqrt{\frac{E}{12\rho(1-v^2)}}$$

With $\lambda_n$ a parameter that is a function of the mode, t the thickness of the membrane, r the radius of the membrane, E the Young's modulus, ρ the density of the material of the membrane and v the Poisson coefficient of the membrane.

Alternatively, finite element modelling may also make it possible to dimension the vibrating device in order to obtain the frequencies of the different modes. FEM software such as Coventor®, COMSOL® or ANSYS® may be used.

For example, a membrane may have a radius comprised between several µm, typically 5 µm, and several hundreds of µm, for example 5000 µm. The thickness may be several tens of nm to several µ.m. As an example, a membrane may have a radius of 500 µm and a thickness of 6 µm.

Only as an example, a membrane having a diameter of 1 cm may make it possible to sort around 1 million cells, for example 500,000 cells of each type.

Circular membranes may have numerous modes, the shapes of which are given for example in FIG. 8. i is the number of nodal diameters and j is the number of nodal circles without counting the built in installation in the periphery of the membrane, λij is a coefficient which is a function of the considered mode.

Each of these modes may be used to sort cell populations. It is thus easy to adapt the vibrations of the membrane to the types of cells to sort.

As has already been mentioned above, the vibrating support may have any shape, it may for example be formed by a vibrating beam anchored into a substrate at one of its ends.

Figure 3:
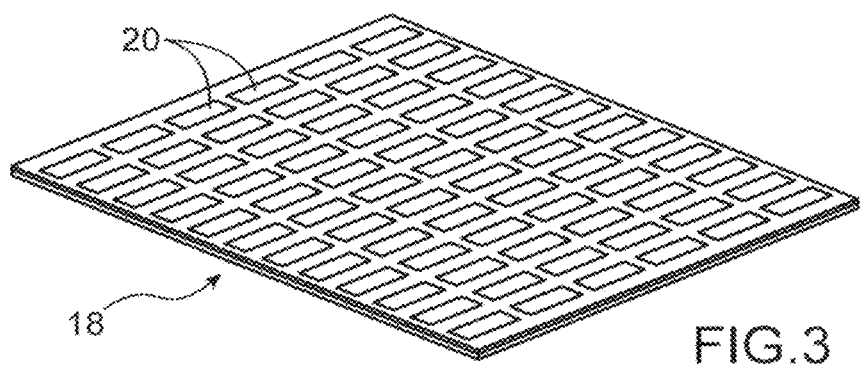
FIG. 3 is a three-quarters view of another example of support provided with several actuators.

In an example of embodiment represented in FIG. 3, the support 18 is formed by a rectangular shaped plate. The plate may be fixed on its edge on one to 4 sides, or be fixed uniquely by fixation points, of double face sticky tape type or fixation notches, positioned at nodal points. It may also be made to vibrate by one or more piezoelectric actuators 20. The rectangular plate may be made to vibrate in its Lamb mode. This configuration makes it possible to have a vibration amplitude and thus a mapping of the force applied to the cells which is homogeneous on the surface. Thus a homogeneous disbonding of the cells is assured over the whole surface of the plate. For example the actuators are positioned so as to favour the sought after mode(s). FEM calculation may advantageously be used to optimise the position and the dimensions of the actuators.

In FIG. 3, the actuators are arranged in line perpendicularly to the length of the plate.

Generally speaking, the vibrating support may comprise one or more rows of actuators, each row comprising at least one actuator. The actuators of a row are separated from each other by a given distance.

For example, a vibrating support may comprise a column of several actuators separated by a space of 500 µm, the actuators being arranged on an antinode, which corresponds to a maximum zone of vibration of the support.

The plate is dimensioned so as to deliver the frequency and the resonance mode suited to detach the cell family concerned.

As an example, an example will now be given of dimensioning of a device making it possible to sort two separate families of cells on a glass plate made to vibrate by PZT actuators:

fibroblasts (NIH/3T3) having adherence forces of the order of 369 nN on glass, keratinocytes having adherence forces of the order of 20 nN.

Using equation (I), it is possible to approximate that from an amplitude of deformation of 1.5 µm, a vibration mode at around 24.5 kHz will disbond the fibroblasts and a vibration mode at around 5 kHz will disbond the keratinocytes.

The vibrating support making it possible to sort the fibroblasts and the keratinocytes may have the following characteristics: it comprises a glass plate having a length of 82 mm, a width of 61 mm and a thickness of 700 µm. It comprises six actuators per row, each actuator being of rectangular shape of which the length extends along the width of the plate. The actuators have a length of 9 mm and a width of 5 mm. The distance separating two lines of actuators is 4000 µm.

Modal analyses carried out using finite element computation software, for example Coventor® or Ansys® software, also make it possible to define the dimensions along the three directions of the space inducing the desired frequencies.

In FIG. 4 are represented several vibration modes of a glass plate of 82 mm×61 mm having a thickness of 700 µm of glass. It may be noted that mode 1 at 5.3 kHz makes it possible to disbond keratinocytes and mode 51 at 25.27 kHz makes it possible to disbond fibroblasts.

Thus it is possible to determine the characteristics of the vibrating support made of a given material for disbonding different types of family knowing their adherence force to said given material.

Figure 5:
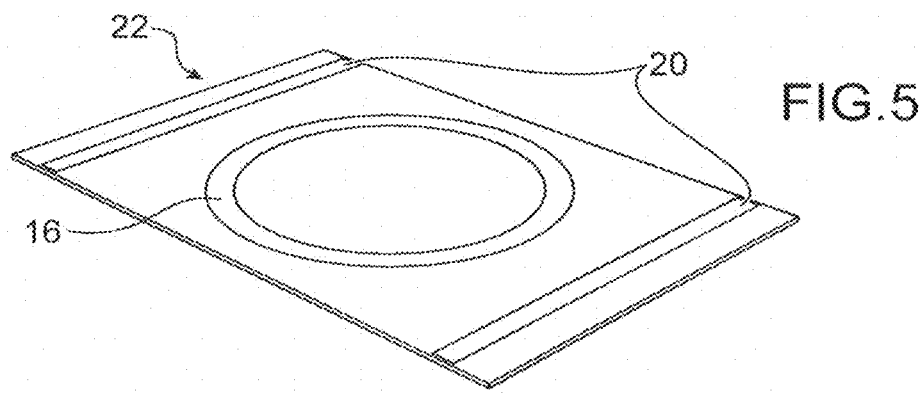
FIG. 5 is a three-quarters view of another example of support provided with several actuators for vibrating in different modes.
Figure 6A:
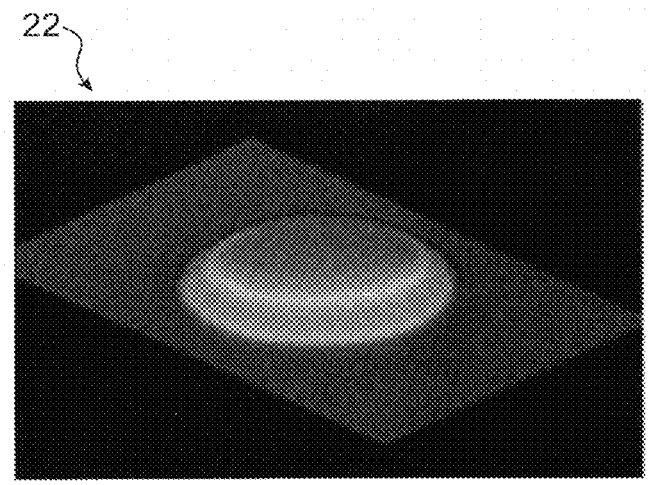
FIGS. 6A and 6B are views of the support of FIG. 5 in different vibration modes.
Figure 6B:
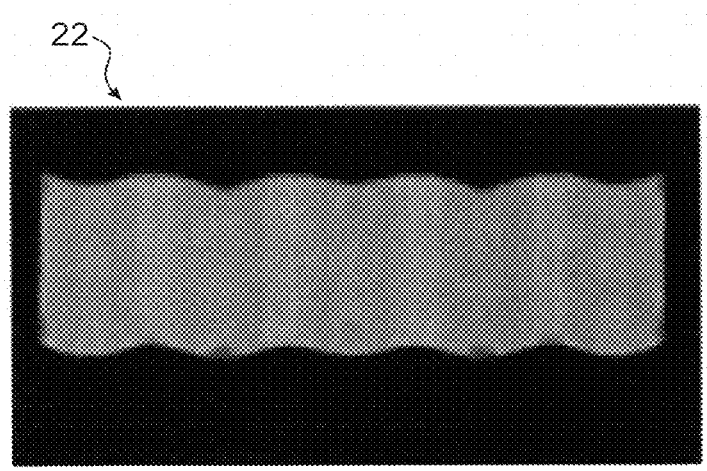

In FIG. 5 may be seen another example of embodiment of a vibrating support 22 according to the invention which associates different types of actuators to generate several vibration modes. In this example, the support is formed by a rectangular plate in the central part comprises an actuator 16 similar to that of a circular membrane for generating a first mode and actuators 20 for generating a Lamb mode similar to those of FIG. 3. In FIG. 6A may be seen the support in a first vibration mode when the actuator 16 is activated and in FIG. 6B may be seen the support in its Lamb mode when the actuators 20 are activated.

Other combinations of actuators may be envisaged.

Each device is designed to make it possible to take one or more types of cells off by applying a given frequency. Nevertheless it may be provided prior to the use of the sorting device to calibrate said device in order to determine precisely at what frequency each of the types of cells detaches from the vibrating support. This calibration is carried out from cells of interest that it is wished to sort with the device. A, B, and C designate the types of cells of interest. The support is formed in such a way that the cells adhere to the surface thereof.

a) According to a first step, the cell population A is introduced into the system. The cells adhere to the support. Then a frequency scanning of the vibrating support is carried out in order to pass through the different modes. The mode and the frequency at which the population A detaches is noted.

The detection of the detached cells may take place for example by microscope observation of the surface considered, by the recovery of the liquid and microscopic analysis of the detached cells or by flow cytometry with a comparison of data before sorting for the evaluation of the sorting purity.

b) During a following step, the same protocol as the first step with the type of B cells is applied.

c) This protocol is resumed with each type of cell of interest. The frequencies of detachment of each of the types of cells of interest for the given sorting device are henceforth known.

d) Then the determined frequencies are checked.

To do so, the biological sample containing the types A, B and C to sort is introduced. The cells adhere to the support.

A frequency scanning is then carried out as a function of the modes determined previously: at each of these modes the populations of cell taken off are recovered to check the purity of the sorting. If each of the populations recovered is pure, the device is correctly calibrated, if not steps a) to d) are repeated. Moreover, it is possible to check whether the cells are living. If this is not the case it is possible to modify the frequency to apply shorter wavelengths and thereby cause the disbonding of focal points and not all the cell in one go, as has been described above. The actuators implemented are capable of generating high frequency vibration modes which have small wavelengths.

The scanning takes place from the lowest frequencies to the highest frequencies in order to avoid taking off all the cells at the same time.

The device with vibrating support according to the invention is particularly suited to implementation in a cell sorting device, said sorting being able to be carried out entirely automatically after a precise calibration of the device.

Nevertheless the device may have other applications, in fact making the support vibrate makes it possible to control the adherence properties of a surface with respect to one or more types of cells. It is thus possible to envisage implementing the invention to prevent cells from adhering thereto or to disbond one or more types of cells to free the surface of the support thereof.

For example, the invention is implemented to produce an active antiadhesive surface for one or more types of cells in a microfluidic circuit. In permanent regime, a sufficiently high frequency of vibration is applied to the surface so that all the types of cells are disbonded. For example, knowing the type of cells having the highest adherence force with respect to the surface, a frequency is applied enabling the disbonding of this type of cells or preventing this type of cells from adhering to the surface, which will cause the disbonding of the other types of cells having a lower adherence force. The surface is thereby protected. The invention has the advantage of offering great adaptability. In fact, it is possible to provide for example during one operating phase to protect one surface while avoiding that any cell adheres to the surface and during another phase to allow all the types of cells to adhere to the surface or certain types of cells.

In controlled regime, it makes it possible to detach cells. For example a control of the surface is carried out, for example an optical control of the surface, to detect undesirable cells having adhered to the surface. If this is the case the support is made to vibrate at the frequency of disbonding undesirable cells and said cells are disbonded. This disbonding is possible if the disbonding frequency of the undesirable cells is lower than those of the cells that it is wished to conserve.

An example of method for producing a sorting device according to the invention will now be described, said device comprising a circular membrane. It is advantageously a method implementing microelectronic techniques, which makes it possible to produce a device suited to the size of cells. Other methods could be envisaged.

Figure 7A:
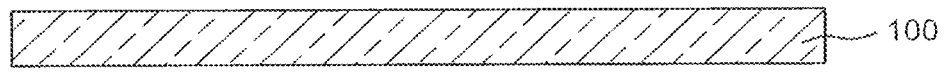
FIGS. 7A to 7S are schematic representations of the elements obtained in the course of different steps of an example of method for producing a sorting device.
Figure 7B:
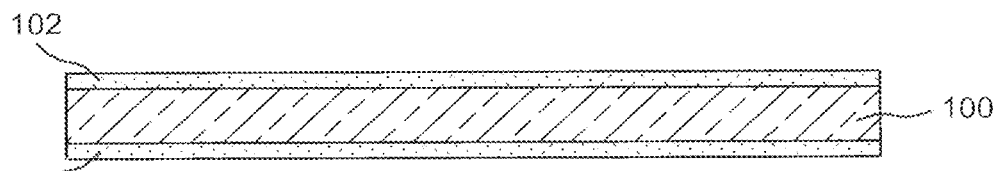
Figure 7C:
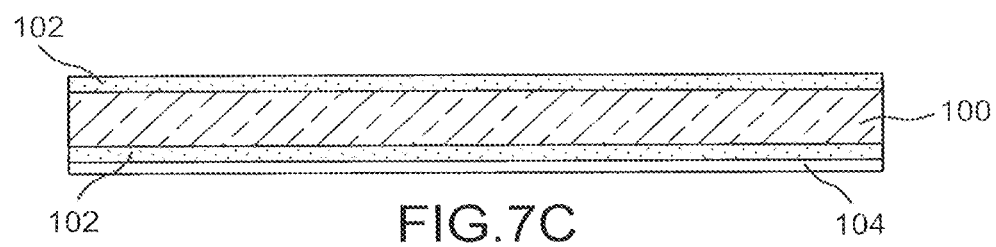
Figure 7D:
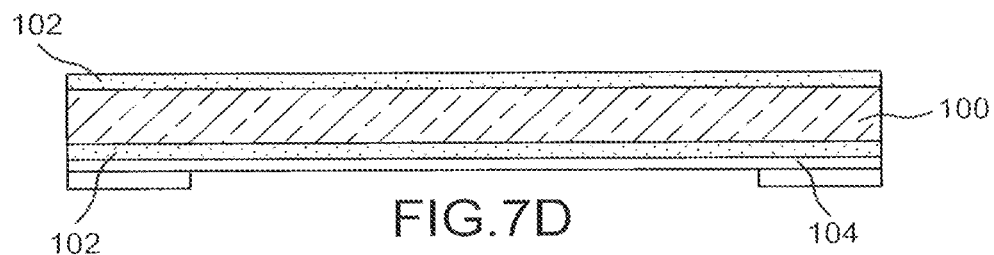
Figure 7E:
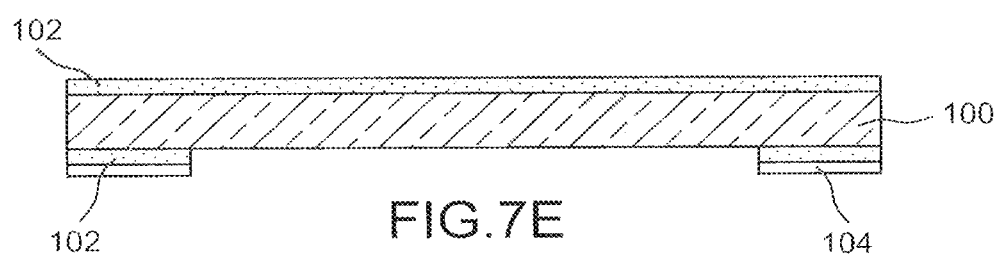
Figure 7F:
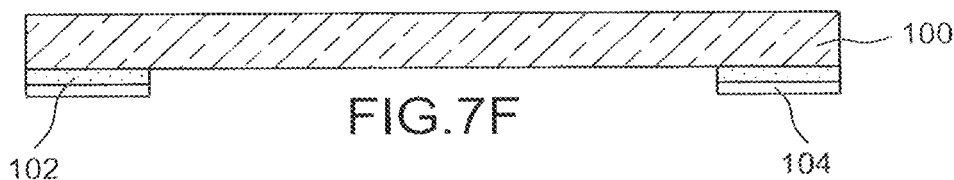
Figure 7G:
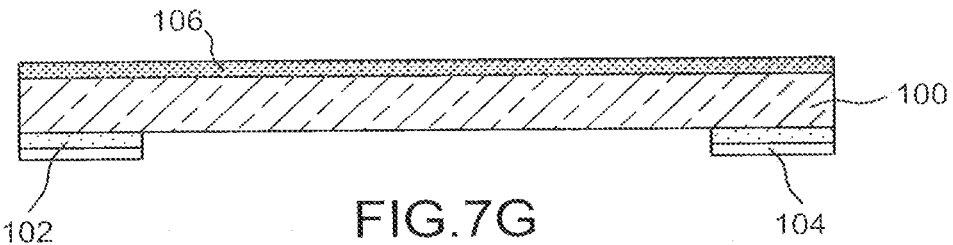
Figure 7H:
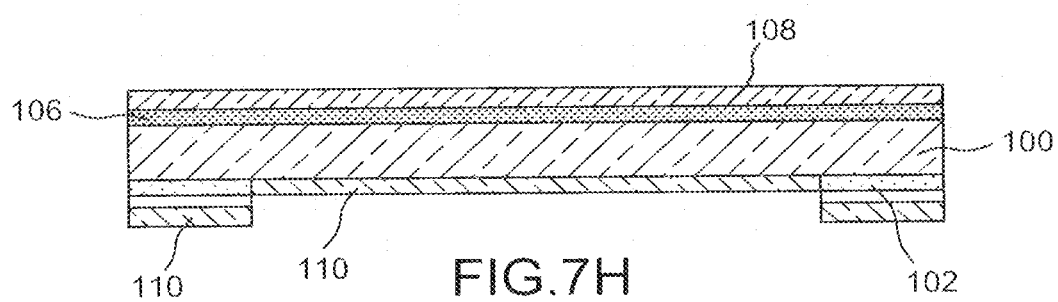
Figure 7I:
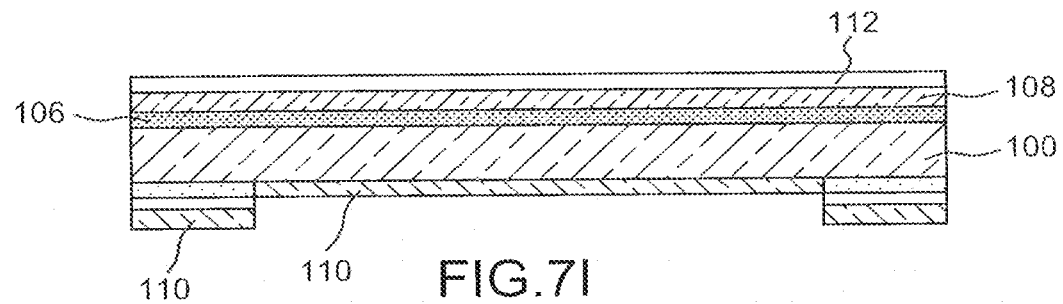
Figure 7J:
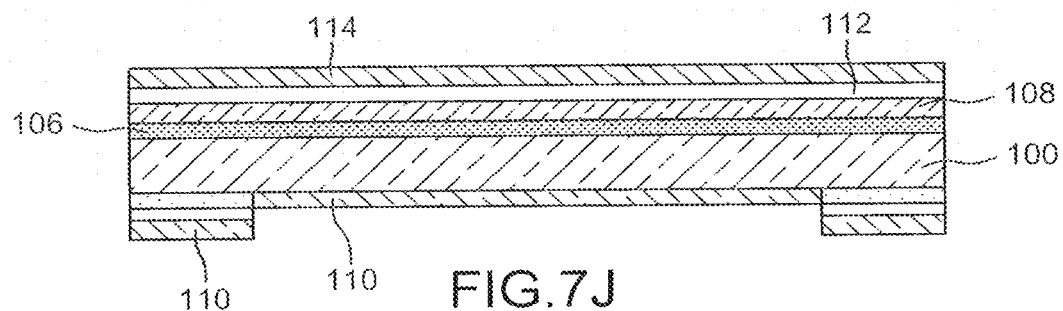
Figure 7K:
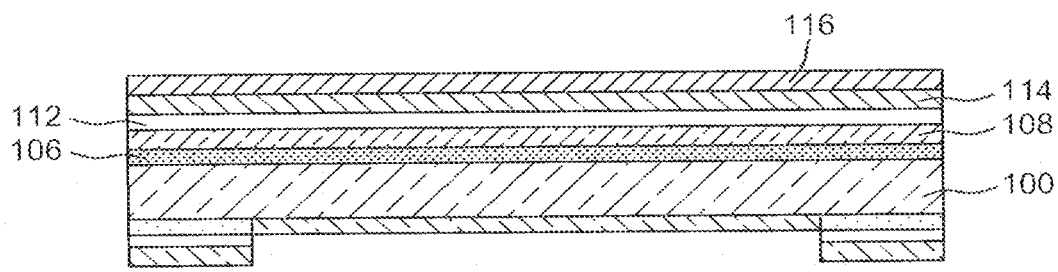
Figure 7L:
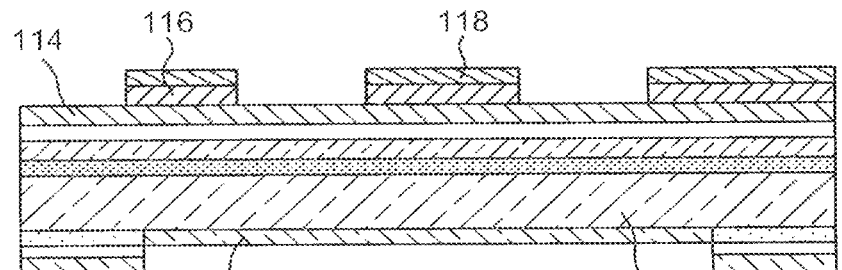
Figure 7M:
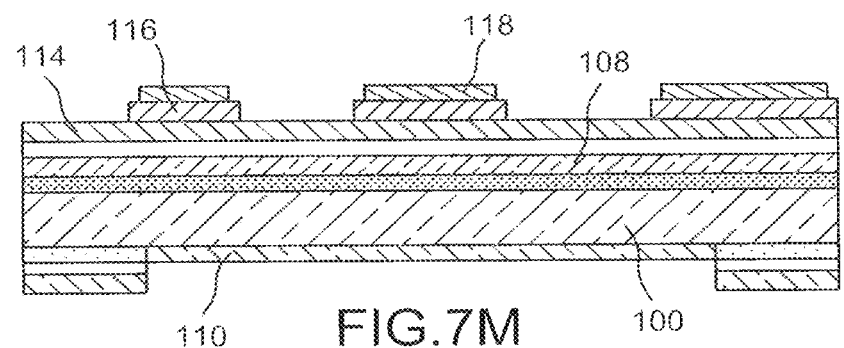
Figure 7N:
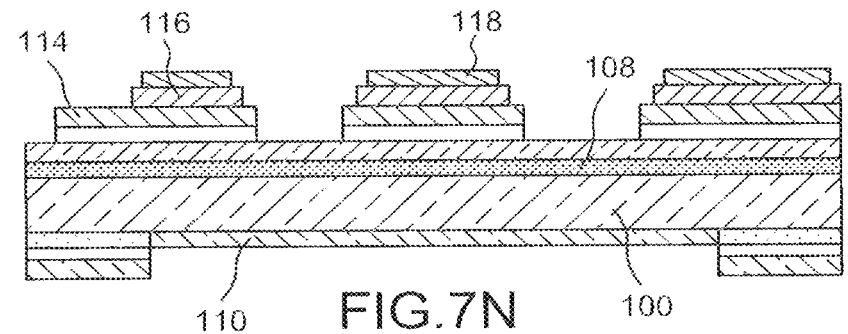
Figure 7O:
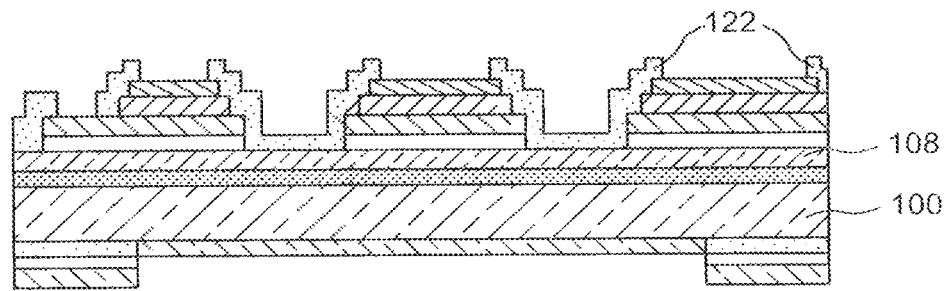
Figure 7P:
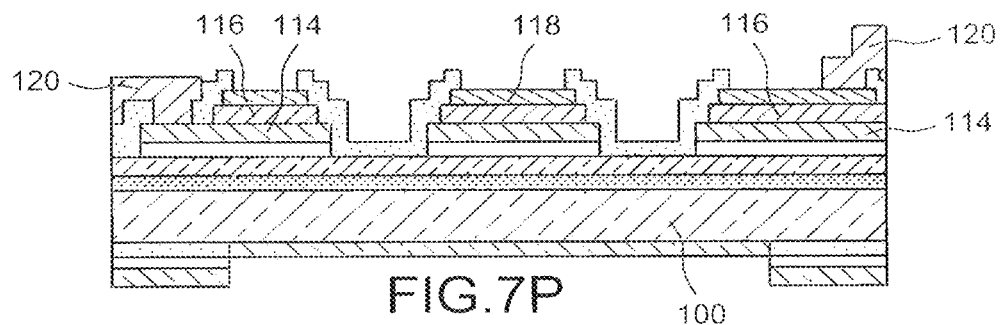
Figure 7Q:
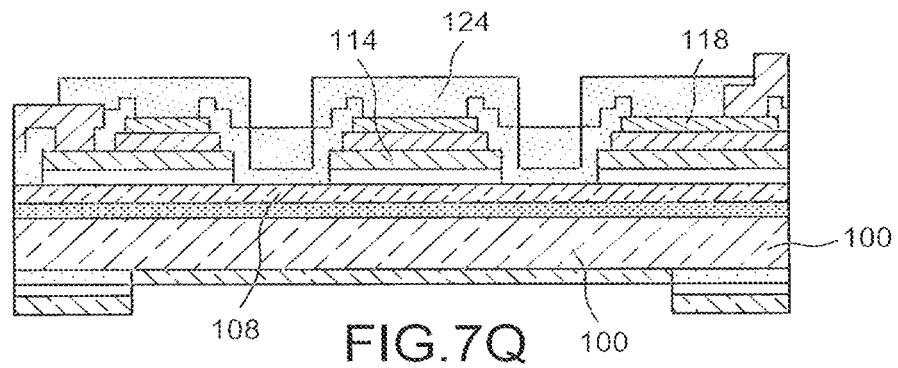
Figure 7R:
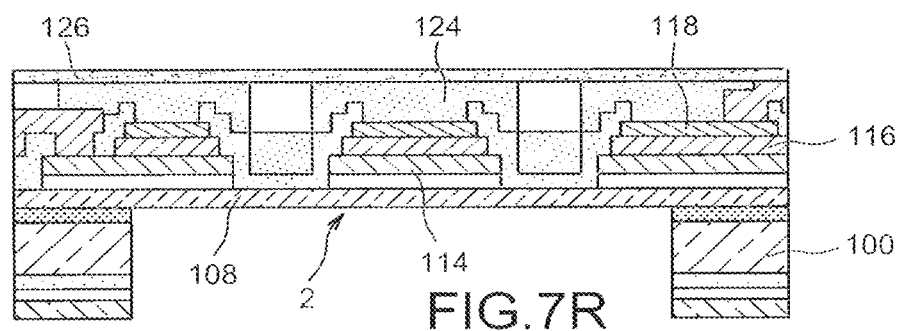
Figure 7S:
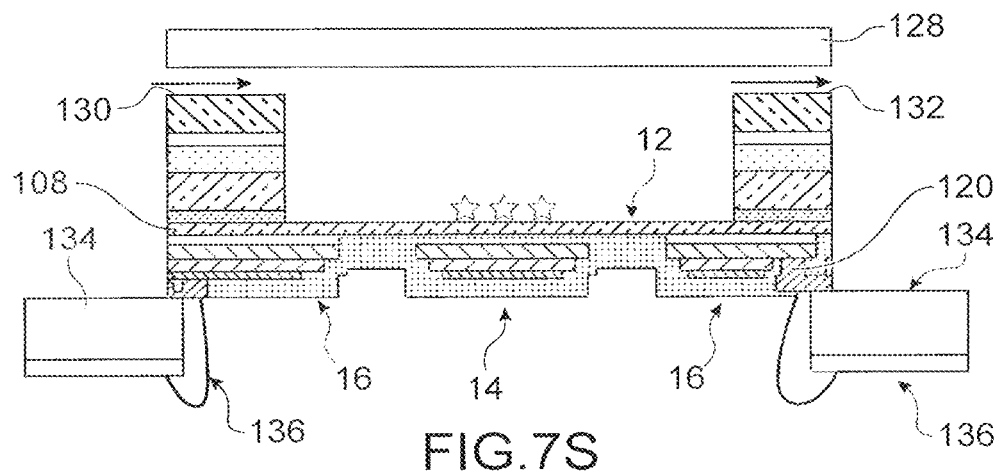

The steps are schematically represented in FIGS. 7A to 7S.

For example, a substrate made of silicon 100 represented in FIG. 7A is used, having for example a thickness of 725 µm and a diameter of 200 mm. A glass substrate for example may be envisaged.

During a first step, a thermal oxidation of the substrate is carried out so as to form a layer of oxide 102 on all the surfaces of the substrate of a thickness of 2 µm for example. The element thereby obtained is represented in FIG. 7B.

Then, a hard mask of oxide 104 is formed on the rear face of the substrate. Said mask has for example a thickness of 7 µm. The mask is formed by turning round the substrate; as a function of the selected deposition composition; it is possible to deposit the mask only on this face. It may be for example a PVD (Physical Vapour Deposition) type deposition. The element thereby obtained is represented in FIG. 7C.

Then a lithography is carried out on the hard mask. The element thereby obtained is represented in FIG. 7D.

During a following step, the hard mask and the layer of oxide 102 on the rear face are etched, for example by reactive-ion etching (RIE), so as to reach the rear face of the substrate 100. The element thereby obtained is represented in FIG. 7E. During a following step, the layer of oxide on the front face is removed, for example by de-oxidation or chemical etching. The element thereby obtained is represented in FIG. 7F.

During a following step, a layer of oxide 106 is formed on the front face. Advantageously, a densification annealing takes place for example at a temperature of the order of 800° C. The element thereby obtained is represented in FIG. 7G.

During a following step, a layer 108 is formed on the front face intended to form the membrane 2, and a layer 110 on the rear face. Preferably, said layers are for example made of polysilicon, SiC or $SiO_2$. The thickness of the layers 108, 110 is for example comprised between several hundreds of nm to several µm, or even several tens of µm.

The layers 108, 110 are for example formed by CVD (Chemical Vapour Deposition) or by epitaxial growth. Preferably, the stresses of the layers 108, 110 are controlled.

The layers 108, 110 may be formed in several stages. For example, for a thickness of 4 µm, two layers of 1.5 µm thickness and 1 layer of 1 µm thickness are formed successively.

Advantageously an annealing step then takes place. The element thereby obtained is represented in FIG. 7H.

During a following step, a layer 112 is formed on the layer 108, for example made of $SiO_2$ or SiN, having for example a thickness comprised between several hundreds of nm and several µm. The layer 112 is formed for example by thermal oxidation or by CVD. Advantageously, a densification annealing takes place for example at a temperature of the order of 800° C.

The element thereby obtained is represented in FIG. 7I.

During a following step, the first and second actuators are formed.

To do so firstly a layer 114 is formed intended to form the lower electrodes of the actuators, for example made of Pt or Mo. The layer 114 is formed for example by deposition on the layer 112. The layer 114 has for example a thickness comprised between several tens of nm to several hundreds of nm. The element thereby obtained is represented in FIG. 7J.

A layer of piezoelectric material 116 is then formed on the layer 114, for example made of PZT, AlN, ZnO, LNO the thickness of which is for example comprised between several hundreds of nm to several µm.

Then the upper electrode is formed by formation of a layer 118 on the piezoelectric material 116, for example made of Ru or Au for example of thickness comprised between several tens of nm to several hundreds of nm. The element thereby obtained is represented in FIG. 7K.

Etching steps then take place.

Firstly, the layer 118 is etched so as to delimit the annular actuator 8 and the disc-shaped actuator 10.

Then, the layer 116 made of piezoelectric material is etched.

The element thereby obtained is represented in FIG. 7L.

Then, the remaining portions of layer 118 are again etched so that they are set back with respect to the portions of layer 116.

The layer 114 is then etched, as well as the layer of oxide 112. The element thereby obtained is represented in FIG. 7M.

Preferably, a stepped profile is formed. This is obtained because all the layers are deposited then etched, from the upper layer, by using different photolithography masks, the second mask being larger than the first, etc. This makes it possible to leave safety margins to avoid covering layers, which could arise on account of the uncertainty of positioning of the masks. Any electrical short circuit between the electrodes is thereby avoided. The element thereby obtained is represented in FIG. 7N.

During following steps, contact pick up pads 120 are formed. Beforehand, a layer 122 of dielectric material is formed, for example made of $SiO_2$ on the edges of stacks formed of lower, upper electrodes and piezoelectric material, this layer being etched so as to free partially the lower and upper electrodes. The element thereby obtained is represented in FIG. 7O.

Then, a layer for example made of AlSi or TiAu is formed and is etched, thereby forming contact pads at the level of the zones where the electrodes have been freed. The element thereby obtained is represented in FIG. 7P.

Advantageously, during a following step a protective layer 124 is formed on the actuators, for example a layer of oxide, in order to protect the actuators from contact with the stop elements. The thickness of said layer may be comprised between several hundreds of nm to several µm, for example 500 nm.

During a following step the layer 124 is etched, in order to access the contact pick-ups.

The element thereby obtained is represented in FIG. 7Q.

Preferably, during a following step, the actuators are protected, for example by the deposition of a dry film 126. Then, the rear face is etched in order to free the membrane 2.

The membrane is released by deep etching of the substrate via the rear face until the membrane is reached.

The element thereby obtained is represented in FIG. 7R.

In order to be able to be used in liquid medium, a suitable packaging is realised. The cavity formed on the side of the rear face of the membrane is closed by a cover 128. In fact preferentially the rear face of the membrane is used to carry out the sorting of the cells, which simplifies the electrical connections of the actuators situated on the front face. Nevertheless since the actuators are encapsulated, the front face provided with actuators may also serve for sorting by adapting the electrical connections. By using both the rear face and the front face, the sorting capacity of the device is doubled. The two faces of the membrane may have the same adherence properties with respect to the different types of cells or different properties, to do so it is possible to functionalise one of the faces.

The cover 128 is for example made of glass and is for example bonded onto the layer 110. It is provided that the cover comprises an inlet orifice 130 and an outlet orifice 132 for the liquid containing the cells Moreover, the device is arranged on supports 134 so as to suspend the membrane and to enable it to vibrate. The supports may be mechanical supports or a part of an electronic circuit board. Advantageously, the supports are also used for the electrical supply using microelectrical connections 136. The microelectrical connections are obtained for example by extending microwires, for example made of gold, which are welded onto the contact pad on one side, and onto the electronic card on the other side.

The element thereby obtained is represented in FIG. 7S. The cells are symbolised by stars.

The device may form part of a microdevice, for example it may form a part of the surface of a microfluidic chamber in the case of a sorting device. It may form part of a microfluidic circuit and assure the protection of the inside of certain of the channels.

In the example represented in FIG. 7S, the vibrating support forms the bottom of the chamber but this is in no way limiting and it may form a lateral wall or even an upper wall. It will then be checked that these walls actually enter into contact with the solution including the cells.

Moreover, it is possible to envisage that a sorting device comprises several separate vibrating supports, making it possible for example to sort one type of cells per vibrating support.

Thanks to the invention, a device is formed having adherence properties which can be modified for different types of cells making it possible to manage said different types of cells.

The invention claimed is:

1. Device for manipulating biological cells distinguished by their adherence properties, comprising:
    at least one support including a reception surface enabling the adherence of a plurality of cells having different adherence properties with respect to said reception surface, the support being a suspended membrane,
    at least one actuator contacting said suspended membrane and configured to make said surface vibrate at at least one natural frequency of the membrane, and
    a controller configured to control said actuator such that the surface vibrates at a predetermined frequency correlated to adherence properties of at least one type of biological cells among said plurality of cells such that the predetermined frequency causing detachment of the at least one type of biological cells while not causing detachment of others of said plurality of cells.

2. Device for manipulating biological cells according to claim 1, the biological cells being of several types, in which the controller is configured to control the actuator such that it makes said surface vibrate at several different frequencies, each of the different frequencies being correlated to adherence properties of a different type of said plurality of cells and selected so as to cause the detachment of at least one selected type among the plurality of the types of biological cells.

3. Device for manipulating biological cells according to claim 1, wherein the predetermined frequency is selected such that vibration waves generated correspond to deformations of the surface of the order of the size of the biological cells or smaller than the size of the biological cells.

4. Device for manipulating biological cells according to claim 1, wherein said actuator is configured to make the surface vibrate at several frequencies, said different frequencies being applied to said surface sequentially.

5. Device for manipulating biological cells according to claim 1, in which all or part of the surface is functionalised so as to modify the adherence force of the type(s) of biological cells with respect to the non-functionalised surface.

6. Device for manipulating biological cells according to claim 1, in which the largest dimension in a plane of the membrane is between several μm and several hundreds of μm.

7. Device for manipulating biological cells according to claim 1, wherein the controller is configured to control the actuator such that the support vibrates in a Lamb mode.

8. Device for manipulating biological cells according to claim 1, comprising several actuators distributed on or under the surface of the support.

9. Device for manipulating biological cells according to claim 8, wherein the controller is configured to control the actuators such that each actuator makes the surface of the support vibrate according to a different mode.

10. Device for manipulating biological cells according to claim 1, each of the at least one actuators are selected from piezoelectric, ferroelectric, electrostatic, magnetic or thermal actuators.

11. Device for manipulating biological cells according to claim 1, wherein the actuator is formed on one face of the support opposite to the receiving surface intended to enter into contact with the biological cells.

12. Device for manipulating biological cells according to claim 1, wherein said device being a MEMS and/or NEMS device.

13. Device for manipulating biological cells according to claim 6, wherein the largest dimension in a plane of the membrane is between 5 μm and 20,000 μm.

14. Device for manipulating biological cells according to claim 1, wherein the at least one actuator contacts said suspended membrane.

15. Microfluidic device comprising:
    at least one device for manipulating biological cells according to claim 1;
    at least one supply inlet with a solution comprising at least one type of biological cells; and
    at least one evacuation outlet, wherein the support being arranged between the supply inlet and the evacuation outlet.

16. Sorting device for sorting biological cells, the sorting device comprising at least one device for manipulating biological cells according to claim 1.

17. Microfluidic device comprising:
    at least a sorting device according to claim 16;
    at least one supply inlet with a solution comprising at least one type of biological cells; and
    at least one evacuation outlet, wherein the support being arranged between the supply inlet and the evacuation outlet.

18. Method for sorting different types of biological cell contained in a solution implementing the sorting device according to claim 16, comprising the steps:
    bringing the solution containing the different types of biological cell into contact with the surface of the support,
    adherence of cells of different types on the surface of the support,
    making the surface vibrate at at least one given frequency so as to detach at least one of the types of cells,
    evacuation of the detached cells.

* * * * *